United States Patent [19]

Lin et al.

[11] 4,433,178

[45] * Feb. 21, 1984

[54] PROCESS FOR PREPARING ACETALDEHYDE FROM METHANOL AND SYNTHESIS GAS USING A NOVEL CATALYST COMPOSITION

[75] Inventors: Jiang-Jen Lin, Round Rock; John F. Knifton, Austin, both of Tex.

[73] Assignee: Texaco, Inc., White Plains, N.Y.

[ * ] Notice: The portion of the term of this patent subsequent to Feb. 21, 2001 has been disclaimed.

[21] Appl. No.: 344,430

[22] Filed: Feb. 1, 1982

[51] Int. Cl.$^3$ .............................................. C07C 47/06
[52] U.S. Cl. .................... 568/487; 568/489; 568/890; 568/902
[58] Field of Search ............... 568/487, 489, 890, 902

[56] References Cited

U.S. PATENT DOCUMENTS

| | | | |
|---|---|---|---|
| 3,285,948 | 11/1966 | Butter | 568/487 |
| 4,151,208 | 4/1979 | Pretzer et al. | 568/487 |
| 4,239,924 | 12/1980 | Pretzer et al. | 568/487 |
| 4,306,091 | 12/1981 | Gauthier-Lafaye | 568/487 |
| 4,348,541 | 9/1982 | Doyle | 568/487 |

*Primary Examiner*—Werren B. Lone
*Attorney, Agent, or Firm*—Carl G. Ries; Jack H. Park; Walter D. Hunter

[57] ABSTRACT

Acetaldehyde is prepared in good yield from methanol and synthesis gas by contacting the mixture of methanol, carbon monoxide and hydrogen with an iodide or iodine-free catalyst composition comprising ruthenium powder, a cobalt-containing compound and an onium salt or base, and heating the resulting mixture to an elevated temperature and pressure for sufficient time to produce the acetaldehyde, and then recovering the same from the reaction mixture.

16 Claims, No Drawings

PROCESS FOR PREPARING ACETALDEHYDE FROM METHANOL AND SYNTHESIS GAS USING A NOVEL CATALYST COMPOSITION

BACKGROUND OF THE INVENTION

1. Field of the Invention

This invention relates to a new process for preparing acetaldehyde. More particularly, the invention relates to a new process for preparing acetaldehyde from methanol and synthesis gas using a novel catalyst composition.

Specifically, the invention provides a new and improved process for preparing acetaldehyde from methanol and syngas in good yields, which process comprises contacting a mixture of methanol, carbon monoxide and hydrogen with an iodide or iodine-free catalyst composition comprising ruthenium powder, a cobalt-containing compound and an onium salt or base, and heating the resulting mixture to an elevated temperature and pressure for sufficient time to produce the acetaldehyde, and then recovering the same from the reaction mixture.

2. Description of the Prior Art

Acetaldehyde is an important chemical of commerce used in a great variety of applications, such as, for example, in the preparation of acetic acid, vinyl acetate, chloral, cyanohydrins and polyhydric alcohol derivatives, such as the glycol monoalkyl ethers. Acetaldehyde has been produced heretofore by methods, such as the hydration of acetylene or the oxidation of ethylene. Such methods, however, have their limitations, particularly, as to cost, and it would be desirable to find a more economical method for producing this compound.

U.S. Pat. No. 4,151,208 discloses a method for producing acetaldehyde from methanol and syngas using a catalyst comprising a special cobalt compound and an iodine promoter. This process, however, is limited because of the serious corrosion problems due to the presence of the iodine promoter. U.S. Pat. No. 4,201,868 discloses a process for preparing a mixture of products containing acetaldehyde using a catalyst comprising a cobalt carbonyl and an organic nitrogen containing ligand. This process is limited by its poor selectivity.

It is an object of the invention, therefore, to provide a new and improved process for preparing acetaldehyde. It is a further object to provide a process for preparing acetaldehyde from methanol and syngas using a new and improved catalyst system. It is a further object to provide a new process for preparing acetaldehyde from methanol and syngas which gives good selectivity and yield of the desired product. It is a further object to provide a process for preparing acetaldehyde which utilizes a catalyst system which is free of corrosive elements and is thus capable of being used on a commercial scale. These and other objects of the invention will be apparent from the following detailed description thereof.

SUMMARY OF THE INVENTION

It has now been discovered that these and other objects may be accomplished by the process of the invention comprising contacting methanol, carbon monoxide and hydrogen with an iodide or iodine-free catalyst composition comprising ruthenium powder, a cobalt-containing compound and an onium salt or base, and heating the resulting mixture to an elevated temperature and pressure for sufficient time to produce the desired acetaldehyde, and then recovering the same from the reaction mixture. It was surprising to find that this new catalyst system was highly selective for the conversion of the methanol to the desired acetaldehyde in view of the discouraging results obtained wih related catalyst systems. A further advantage of the process being that it avoids the use of catalysts which contain corrosive elements, such as iodide or iodine compounds and is thus suited for use on a commercial scale.

As disclosed and claimed in our copending patent application Ser. No. 344,260 filed this same date Feb. 1, 1982, it has been surprisingly found that even higher selectivity in the formation of the acetaldehyde can be obtained by including an amine promoter in the aforementioned catalyst system.

As further disclosed and claimed in our copending patent application Ser. No. 344,429 filed this same date Feb. 1, 1982, it has also been surprisingly found that the reaction conditions of the above-noted process can be greatly improved by the addition of a rhodium-containing compound with the aforementioned catalyst system. The addition of such compounds, for example, permits the use of such milder pressures than generally required for the high production selectivity in the formation of the acetaldehyde.

As noted, the process of the present invention is particularly characterized by the good selectivity in the conversion of the methanol and syngas to acetaldehyde as represented by the following equation:

$$CH_3OH + CO + H_2 \rightarrow CH_3CHO + H_2O \qquad (1)$$

Typical conversions of the methanol to acetaldehyde range from about 58% to about 94% with selectivity to acetaldehyde of ca. 50%. Valuable by-products of the reaction include ethanol, methyl acetate, ethyl acetate, and the like.

DETAILED DESCRIPTION OF THE INVENTION

In the operation of the process of the invention, the acetaldehyde, along with the above-noted by-products, are produced concurrently from the methanol and syngas by a process comprising the following steps:

(a) contacting a mixture of the methanol, carbon monoxide and hydrogen with a catalyst composition comprising ruthenium metal powder, a cobalt-containing compound and an onium salt or base, said reaction mixture can and sometimes preferably does contain a solvent, such as p-dioxane, (b) heating the said mixture to an elevated temperature, e.g. above 150° C. and an elevated pressure, e.g. above 500 psi, with sufficient carbon monoxide and hydrogen to satisfy the stoichiometry of the desired acetaldehyde synthesis as noted above, until formation of the desired acetaldehyde has been achieved, and (c) preferably isolating the said acetaldehyde and minor by-products from the reaction mixture, as by distillation.

In order to present the inventive concept of the present invention in the greatest possible detail, the following supplementary disclosure is submitted. The process of the invention is practiced as follows.

As noted, the new catalyst system used in the process of the invention contains ruthenium metal powder, a cobalt-containing compound and an onium salt or base.

The ruthenium metal powder can be powdered ruthenium metal of any mesh size.

The cobalt-containing compound to be used in the catalyst composition may take many different forms. For instance, the cobalt may be added to the reaction mixture in the form of an oxide, salt, carbonyl derivative and the like. Examples of these include, among others, cobalt oxides $Co_2O_3$, $Co_3O_4$, CoO, cobalt(II) bromide, cobalt(II) thiocyanate, cobalt(II) hydroxide, cobalt(II) carbonate, cobalt(II) nitrate, cobalt(II) phosphate, cobalt acetate, cobalt naphthenate, cobalt benzoate, cobalt valerate, cobalt cyclohexanoate, cobalt carbonyls, such as dicobalt octacarbonyl $Co_2(CO)_8$, tetracobalt dodecacarbonyl $Co_4(CO)_{12}$ and hexacobalt hexadecacarbonyl $Co_6(CO)_{16}$ and derivatives thereof by reaction with ligands and preferably group V donors, such as the phosphines, arsines and stilbines, such as $(Co(CO)_3L)_2$ wherein L is $PR_3$, $AsR_3$ and $SbR_3$ wherein R is a hydrocarbon radical, cobalt carbonyl hydrides, cobalt carbonyl bromide, cobalt nitrosyl carbonyls as $CoNO(CO)_3$, $Co(NO)(CO)_2PPh_3$, cobalt nitrosyl bromides, organometallic compounds obtained by reacting cobalt carbonyls with olefins, allyl and acetylene compounds, such as bis($\pi$-cyclopentadienyl) cobalt $(\pi C_5H_5)_2Co$, cyclopentadienyl cobalt dicarbonyl, bis(hexamethylenebenzene) cobalt.

Preferred cobalt-containing compounds to be used in the catalyst system comprise those having at least one cobalt atom attached to carbon, such as the cobalt carbonyls and their derivatives as, for example, dicobalt octacarbonyl, tetracobalt dodecacarbonyl, $(Co(CO)_3P(CH_3)_3)_2$, organometallic compounds obtained by reacting the cobalt carbonyls with olefins, cycloolefins, allyl and acetylene compounds such as cyclopentadienyl cobalt dicarbonyl, cobalt carbonyl bromides, cobalt carbonyl hydrides, cobalt nitrosyl carbonyls, and the like, and mixtures thereof.

Particularly preferred cobalt-containing compounds to be used in the catalyst comprise those having at least one cobalt atom attached to at least three separate carbon atoms, such as for example, the dicobalt octacarbonyls and their derivatives.

The quaternary onium salt or base to be used in the catalyst composition may be any onium salt or base, but are preferably those containing phosphorous or nitrogen, such as those of the formula

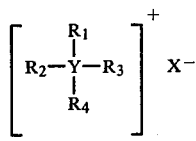

wherein Y is phosphorous or nitrogen, $R_1$, $R_2$, $R_3$ and $R_4$ are organic radicals, preferably alkyl, aryl or alkaryl radicals, and X is an anionic species. The organic radicals useful in this instance include those alkyl radicals having from 1 to 20 carbon atoms in a branched or linear alkyl chain, such as methyl, ethyl, n-butyl, isobutyl, octyl, 2-ethylhexyl and dodecyl radicals. Tetraethylphosphonium bromide and tetrabutylphosphonium bromide are typical examples presently in commercial production. The corresponding quaternary phosphonium or ammonium acetates, hydroxides, nitrates, chromates, tetrafluoroborates and the corresponding chlorides are also satisfactory.

Equally useful are the phosphonium and ammonium salts containing phosphorous or nitrogen bonded to a mixture of alkyl, aryl and alkaryl radicals, which radicals preferably contain from 6 to 20 carbon atoms. The aryl radical is most commonly phenyl. The alkaryl group may comprise phenyl substituted with one or more $C_1$ to $C_{10}$ alkyl substituents, bonded to phosphorous or nitrogen through the aryl function.

Illustrative examples of suitable quaternary onium salts or bases include tetrabutylphosphonium bromide, n-heptyltriphenylphosphonium bromide, tetrabutylammonium chloride, tetrabutylphosphonium nitrate, tetrabutylphosphonium hydroxide, tetrabutylphosphonium chromate, tetraoctylphosphonium tetrafluoroborate, tetrahexyl phosphonium acetate and tetraoctylammonium bromide.

The preferred quaternary onium salts and bases to be used in the process comprise the tetralkylphosphonium salts containing alkyl groups having 1 to 6 carbon atoms, such as methyl, ethyl, butyl, hexyl, heptyl and isobutyl. Tetralkylphosphonium salts, such as the bromides and chlorides acetate and chromate salts and hydroxide base, are the most preferred.

The quantity of the ruthenium powder and the cobalt-containing compound to be used in the process of the invention may vary over a wide range. The process is conducted in the presence of a catalytically effective amount of the active ruthenium powder and the active cobalt-containing compound which gives the desired product in a reasonable yield. The reaction proceeds when employing as little as about $1 \times 10^{-6}$ weight percent, and even lesser amounts of the ruthenium powder, together with as little as about $1 \times 10^{-6}$ weight percent of the cobalt-containing compound, or even lesser amounts, based on the total weight of the reaction mixture. The upper concentration is dictated by a variety of factors including catalyst cost, partial pressures of carbon monoxide, operating temperature, etc. An amount of the ruthenium powder of from about $1 \times 10^{-5}$ to about 5 weight percent in conjunction with a cobalt-containing compound concentration of from about $1 \times 10^{-5}$ to about 5 percent, based on the total weight of the reaction mixture is generally desirable in the practice of this invention. The preferred ruthenium to cobalt atomic ratios are from about 10:1 to 1:10.

Generally, in the catalyst system used in the process of the invention, the molar ratio of the ruthenium powder to the quaternary onium salt or base will range from about 1:0.1 to about 1:100 or more, and preferably will be from about 1:1 to about 1:20.

Particularly superior results are obtained when the above-noted three components of the catalyst system are combined in a molar basis as follows: ruthenium powder 0.1 to 4 moles, cobalt-containing compound 0.1 to 8 moles and the quaternary onium salt or base 0.4 to 60 moles, and still more preferably when the components are combined in the following molar ratios: ruthenium powder 1 to 4 moles, cobalt-containing compound 2 to 4 moles and the quaternary onium base or salt 10 to 50 moles.

Solvents may be and sometimes preferably are employed in the process of the invention. Suitable solvents for the process include the oxygenated hydrocarbons, e.g. compounds possessing only carbon, hydrogen and oxygen and one in which the oxygen atom present is in an ether, ester, ketone carbonyl or hydroxyl group or groups. Generally, the oxygenated hydrocarbon will contain from about 3 to 12 carbon atoms and preferably a maximum of three oxygen atoms. The solvent must be substantially inert under the reaction conditions, must be relatively non-polar and preferably must be one which has a normal boiling point of at least 65° C. at atmospheric pressure and still more preferably the solvent will have a boiling point greater than that of the ester and other products of the reaction so that recovery of the solvent by distillation is facilitated.

Preferred ester type solvents are the aliphatic, cycloaliphatic and aromatic carboxylic acid esters as exemplified by methyl benzoate, isopropyl benzoate, butyl cyclohexanoate, as well as dimethyl adipate. Useful alcohol-type solvents include the monohydric alcohols as cyclohexanol and 2-octanol, etc. Suitable ketone-type solvents include, for example, cyclic ketones, such as cyclohexanone, 2-methylcyclohexanone, as well as acyclic ketones, such as 2-pentanone, butanone, acetophenone, etc. Ethers which may be utilized as solvents include cyclic, acyclic, and heterocyclic materials. Preferred ethers are the heterocyclic ethers as illustrated by 1,4-dioxane and 1,3-dioxane. Other suitable ethers include isopropyl dibutyl ether, diethylene glycol dibutyl ether, diphenyl ether, dibutyl ether, heptyl phenyl ether, anisole, tetrahydrofurane, etc. The most useful solvents of all of the above groups include the ethers, as represented by the polycyclic heterocyclic ethers such as diphenyl ether and 1,4-dioxane, etc.

The amount of the solvent employed may vary over a wide range. In general, it is desirable to use sufficient solvent to fluidize the catalyst system.

The relative amounts of carbon monoxide and hydrogen which may be initially present in the syngas mixture can be varied widely. In general, the mole ratio of CO to $H_2$ is in the range from about 20:1 to 1:20, preferably from about 5:1 to 1:5. Particularly in continuous operations, but also in batch experiments, the carbon monoxide-hydrogen gaseous mixture may also be used in conjunction with up to 50% by volume of one or more other gases. These other gases may include one or more inert gases such as nitrogen, argon, neon and the like, or they may include gases that may or may not undergo reaction under CO hydrogenation conditions, such as methane, ethane, propane, and the like, ethers, such as dimethyl ether and diethyl ether.

The temperature used in the process of the invention may vary over a considerable range. Preferred temperatures range from about 100° C. to about 350° C. The exact temperature selected will depend upon experimental factors, such as the pressure, the concentration and choice of the particular catalyst and cocatalyst selected, etc. Particularly preferred temperatures range from about 150° C. to about 250° C.

Superatmospheric pressures of say at least 500 psi or greater lead to substantial yields of the desired acetaldehyde. In general, pressures varying from about 1000 psi to about 7500 psi give good results and are generally preferred. The pressures referred to herein represent the total pressure generated by all the reactants, although they are substantially due to the carbon monoxide and hydrogen reactants.

The desired product of the reaction, acetaldehyde, will be formed in significant quantities generally varying up to about 46% selectivities. Also formed will be minor by-products including ethanol, methyl and ethyl acetate, and other lower oxygenated products. The acetaldehyde and the by-products can be recovered from the reaction mixture by conventional means, e.g. fractional distillation in vacuo.

The novel process of the invention can be conducted in a batch, semi-continuous or continuous manner. The catalyst can be initially introduced into the reaction zone batchwise, or it may be continuously or intermittently introduced into such a zone during the course of the synthesis reaction. Operating conditions can be adjusted to optimize the formation of the desired acetaldehyde product, and said material may be recovered by methods known to the art, such as distillation, fractionation, extraction and the like. A fraction rich in the catalyst components may then be recycled to the reaction zone, if desired, and additional product generated.

The products have been identified in this work by one or more of the following analytical procedures; viz, gas-liquid phase chromatography (glc), infrared (ir) mass spectrometry, nuclear magnetic resonance (nmr) and elemental analyses, or a combination of these techniques. Analyses have, for the most part, been by parts by weight; all temperatures are in degree centigrade and all pressures in pounds per square inch (psi).

To illustrate the process of the invention, the following examples are given. It is to be understood, however, that the examples are given in the way of illustration and are not to be regarded as limiting the invention in any way.

EXAMPLE I

This example illustrates the improved results obtained in the production of acetaldehyde from syngas using the new catalyst system.

A glass liner was charged with 0.050 g (0.5 mmole) of ruthenium powder, 0.34 g (1.0 mmole) of dicobalt octacarbonyl, 3.40 g (10.0 mmoles) of tetra-n-butylphosphonium bromide, 6.5 g of methanol and 20 g of p-dioxane. The glass liner was placed in a stainless steel reactor, the reactor was purged of air and pressured to 2000 psi with a mixture of carbon monoxide and hydrogen (1:2 molar) and then heated to 202° C. while it was agitated by rocking. The pressure was brought up to 6300 psi and the constant pressure was maintained by repressuring with additional amounts of the carbon monoxide-hydrogen mixture from a surge tank.

The reaction was terminated after 18 hours and the reactor was cooled to room temperature (final pressure was 4400 psi.) The off-gas was vented and 32.7 g of reddish liquid was obtained.

The liquid product was analyzed by glc and showed the following product composition:

| | |
|---|---|
| 10.0 wt % | acetaldehyde |
| 1.4 wt % | methanol |
| 2.5 wt % | ethanol |
| 1.7 wt % | methyl acetate |
| 1.9 wt % | ethyl acetate |
| 1.3 wt % | unknown |
| 9.4 wt % | water |
| 68.3 wt % | p-dioxane |

The product selectivities (excluding p-dioxane and water) were calculated to be as follows:

| | |
|---|---|
| 48 wt % | acetaldehyde |
| 12 wt % | ethanol |
| 8 wt % | methyl acetate |
| 9 wt % | ethyl acetate |

The methanol conversion was 94 wt%.

The molar yield of acetaldehyde, based upon the methanol charged, was estimated to be 38 mole %.

EXAMPLE I Comparative Tests

The following experiments demonstrate the surprising nature of the above-noted results in relation to results obtained with other catalyst systems.

The procedure of Example I above was repeated with the exception that no dicobalt octacarbonyl was added to the reaction mixture. The temperature employed was 200° C. and pressure of 6300 psi for 18 hours. At the end of that time no acetaldehyde was detected.

The procedure of Example I above was repeated with the exception that no tetra-n-butylphosphonium bromide was added to the reaction mixture. The temperature employed was 200° C. and pressure of 6300 psi for 18 hours. Only 4% acetaldehyde was detected.

The procedure of Example I above was repeated with the exception that no ruthenium metal powder was added to the reaction mixture. The temperature employed was 200° C. and pressure of 6300 psi for 18 hours. At the end of that time, only 30% methanol conversion and 24% acetaldehyde selectivity were observed.

EXAMPLE II

Example I was repeated with the exception that the catalyst system comprised 1 mmole of ruthenium powder (0.101 g), 1 mmole of dicobalt octacarbonyl (0.34 g) and 10 mmole of tetra-n-butylphosphonium bromide (3.4 g), and 8.0 g of methanol and 24 g of p-dioxane were added to the reaction mixture. Temperature was 200° C. and pressure was 6300 psi for a reaction period of 18 hours.

Analysis of liquid product (40.1 g) showed the following results:

| | |
|---|---|
| 10.8 wt % | acetaldehyde |
| 2.9 wt % | methanol |
| 4.2 wt % | ethanol |
| 2.2 wt % | methyl acetate |
| 1.7 wt % | ethyl acetate |
| 1.3 wt % | unknown |
| 13.7 wt % | water |
| 61.0 wt % | p-dioxane |

The calculated product selectivities (excluding water and solvent, p-dioxane) based on this glc analysis were:

| | |
|---|---|
| 48 wt % | acetaldehyde |
| 19 wt % | ethanol |
| 10 wt % | methyl acetate |
| 8 wt % | ethyl acetate |

The methanol conversion was 88 wt% and the water analysis by Karl-Fisher method was 11.0 wt%.

The yield of acetaldehyde produced, based on the methanol charged, was estimated to be 41 mole %.

EXAMPLE III

The procedure of Example I was repeated with the exception that the catalyst system comprised 0.25 mmole (0.025 g) of ruthenium powder, 0.5 mmole (0.17 g) dicobalt octacarbonyl, 5.0 mmoles (1.7 g) of tetra-n-butylphosphonium bromide and 4.0 g of methanol and 15.0 g of p-dioxane were added to the reaction mixture. Synthesis gas was added in a 2:1 ($H_2$:CO) molar mix. The operating temperature was 200° C. and pressure was 4000 psi for reaction period of 18 hours. The liquid product (21.8 g) was analyzed by glc and showed the following:

| | |
|---|---|
| 6.5 wt % | acetaldehyde |
| 6.0 wt % | methanol |
| 1.2 wt % | ethanol |
| 2.2 wt % | methyl acetate |
| 2.8 wt % | ethyl acetate |
| 6.4 wt % | water |
| 73.4 wt % | p-dioxane |

The product selectivities (excluding p-dioxane and water) were calculated to be:

| | |
|---|---|
| 46 wt % | acetaldehyde |
| 9 wt % | ethanol |
| 15 wt % | methyl acetate |
| 20 wt % | ethyl acetate |

The methanol conversion was 70%.

EXAMPLES IV TO X

The procedures for preparing acetaldehyde of Example I were repeated with various molar ratios of catalyst compositions. The three component catalyst system comprised in each case of ruthenium metal, tetra-n-butylphosphonium bromide and dicobalt octacarbonyl. The ratios of ruthenium to Bu$_4$PBr was varied from 0.5:5 to 0.5 to 40 (see Table I). The ratio of ruthenium metal to cobalt octacarbonyl likewise was varied from 0.5 to 1 to 0.5 to 0.25. The optimal acetaldehyde selectivity was achieved for a ruthenium metal: tetra-n-butylphosphonium bromide:dicobalt octacarbonyl molar ratio of 0.5:20:0.25 (see Example VI).

The results are shown in Table No. I.

TABLE NO. I

| Example | Ru/n-Bu$_4$PBr/Co$_2$(CO)$_8$ (mmole used) | Methanol and Solvent | Reaction Conditions[a] | Methanol Conversion (%) | H$_2$O % by K.F. | Product Selectivities (wt %) | | | | | Wt Gain (g) |
|---|---|---|---|---|---|---|---|---|---|---|---|
| | | | | | | CH$_3$CHO | C$_2$H$_5$OH | CH$_3$OAc | C$_2$H$_5$OAc | HOAc | |
| Example IV | (0.5:5:1) | MeOH 6.4 g p-dioxane 20 g | 6250~5800 psi 200° C., 18 hrs. | 81 | — | 38 | 23 | 5 | 7 | 0 | 2.3 |
| Example V | (0.5:20:1) | MeOH 8 g p-dioxane 25 g | 7250~6500 psi 200° C., 4 hrs. | 80 | 8.56 | 43 | 0 | 17 | 18 | 0 | 4.2 |
| Example VI | (0.5:20:0.25) | MeOH 6.4 g p-dioxane 20 g | 7900~7300 psi 200° C., 4 hrs. | 79 | 5.17 | 48 | 0 | 26 | 15 | 0 | 1.8 |
| Example VII | (0.5:40:1) | MeOH 8 g p-dioxane 20 g | 6300 psi 200° C., 18 hrs. | 100 | 7.91 | 19 | 12 | 4 | 19 | 27 | 6.0 |
| Example | (0.5:5:1) | MeOH 8 g | 6300 psi | 83 | 11.5 | 33 | 42 | 6 | 5 | 0 | 3.0 |

TABLE NO. I-continued

| Example | Ru/n-Bu₄PBr/Co₂(CO)₈ (mmole used) | Methanol and Solvent | Reaction Conditions(a) | Methanol Conversion (%) | H₂O % by K.F. | Product Selectivities (wt %) | | | | | Wt Gain (g) |
|---|---|---|---|---|---|---|---|---|---|---|---|
| | | | | | | CH₃CHO | C₂H₅OH | CH₃OAc | C₂H₅OAc | HOAc | |
| Example VIII | | p-dioxane 20 g | 200° C., 18 hrs. | | | | | | | | |
| Example IX | (0.5:5:1) | MeOH 8 g p-dioxane 20 g | ~6400 psi 200° C., 4 hrs. | 69 | 6.96 | 41 | 0 | 6 | 44 | 0 | 3.6 |
| Example X | (0.5:5:0.25) | MeOH 3.1 g p-dioxane 10 g | 6300~5500 psi 200° C., 18 hrs. | 92 | — | 41 | 15 | 15 | 10 | 0 | 1.0 |

(a)CO/H₂ = 1:2
(b)n-Bu₄PBr = tetrabutylphosphonium bromide
MeOH = methanol
CH₃OAc = methyl acetate
C₂H₅OAc = ethyl acetate
HOAc = acetic acid
CH₃CHO = acetaldehyde
Ru = ruthenium metal powder

EXAMPLE XI

This example illustrates the use of n-heptyltriphenylphosphonium bromide as the onium salt.

A glass liner was charged with 0.5 mmole of ruthenium metal powder, 1 mmole of dicobalt octacarbonyl, 5 mmole of n-heptyltriphenylphosphonium bromide, 8.0 g of methanol and 20 g of p-dioxane. The glass liner was placed in a stainless steel reactor, the reactor was purged of air and pressured to 2000 psi with a mixture of carbon monoxide and hydrogen (1:2 molar ratio) and then heated to 200° C. while it was agitated by rocking. The pressure was brought up and maintained at 6000 psi. The reaction was terminated after 18 hours and the reactor was cooled to room temperature. Analysis of the resulting liquid product was by glc. Product selectivities were estimated as follows:

| |
|---|
| 46% by weight acetaldehyde |
| 35% by weight ethanol |
| 3% by weight ethyl acetate |

Conversion of methanol was 75%.

What is claimed is:

1. A process for preparing acetaldehyde from methanol and syngas which comprises contacting a mixture of methanol, carbon monoxide and hydrogen with a catalytic amount of an iodine-free catalyst composition comprising ruthenium powder, a cobalt-containing compound, selected from the group consisting of cobalt oxides, cobalt salts, cobalt carbonyls and derivatives of aforesaid, and a quaternary onium compound, selected from the group consisting of quaternary ammonium salts, quaternary ammonium bases, quaternary phosphonium salts and quaternary phosphonium bases, and heating the resulting mixture to a temperature above 150° C. and a pressure above 500 psi for sufficient time to produce acetaldehyde.

2. A process as in claim 1 wherein the cobalt-containing compound is a member of the group consisting of cobalt carbonyls and derivatives thereof obtained by reacting the carbonyls with a group V donor ligand, cobalt carbonyl hydrides, cobalt carbonyl chlorides and bromides, cobalt chlorides and bromides and cobalt salts or organic carboxylic acids.

3. A process as in claim 1 wherein the cobalt-containing compound is a cobalt compound having at least one cobalt atom linked to at least three separate carbon atoms.

4. A process as in claim 1 wherein the quaternary onium salt or base is a tetrahydrocarbylphosphonium salt having from 1 to 10 carbon atoms in each of the hydrocarbyl groups.

5. A process as in claim 4 wherein the salt is selected from the group consisting of tetrahydrocarbylphosphonium bromides, chlorides, and chromates.

6. A process as in claim 1 wherein the catalyst components are utilized in the following molar ratios: ruthenium powder 0.1 to 4 moles; cobalt-containing compound 0.1 to 8 moles; quaternary onium salt or base 0.4 to 60 moles.

7. A process as in claim 1 wherein the carbon monoxide and hydrogen are employed in a molar ratio varying from 5:1 to 1:5.

8. A process as in claim 1 wherein the reaction is conducted at a temperature between 150° C. and 350° C.

9. A process as in claim 1 wherein the reaction is conducted at a pressure between 1000 psi and 7500 psi.

10. A process as in claim 1 wherein the quaternary onium salt or base is tetra-n-butylphosphonium bromide.

11. A process for preparing acetaldehyde from methanol and syngas which comprises contacting a mixture of methanol, carbon monoxide and hydrogen with a catalytic amount of an iodine-free catalyst composition comprising ruthenium powder, a cobalt carbonyl and a quaternary phosphonium salt selected from the group consisting of quaternary tetrahydrocarbylphosphonium chloride and quaternary tetrahydrocarbylphosphonium bromide,, and heating the resulting mixture to a temperature between 150° C. and 350° C. and a pressure between 1000 psi and 7500 psi for sufficient time to produce the desired acetaldehyde and recovering the same from the reaction mixture.

12. A process as in claim 1 wherein a solvent is included in the reaction mixture.

13. A process as in claim 12 wherein the solvent is a heterocyclic ether.

14. A process as in claim 1 wherein dioxane is included in the reaction mixture.

15. A process as in claim 11 wherein the cobalt carbonyl is dicobalt octacarbonyl.

16. A process as in claim 11 wherein the quaternary tetrahydrocarbylphosphonium chloride or bromide is n-heptyltriphenylphosphonium bromide.

* * * * *